(12) United States Patent
Doerr

(10) Patent No.: US 8,249,690 B2
(45) Date of Patent: Aug. 21, 2012

(54) BRAIN STIMULATION ELECTRODE LINE AND INSERTION DEVICE FOR BRAIN STIMULATION ELECTRODE LINES

(75) Inventor: Thomas Doerr, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 492 days.

(21) Appl. No.: 12/406,300

(22) Filed: Mar. 18, 2009

(65) Prior Publication Data

US 2009/0240147 A1     Sep. 24, 2009

(30) Foreign Application Priority Data

Mar. 20, 2008 (DE) .......................... 10 2008 015 156

(51) Int. Cl.
*A61B 5/00* (2006.01)
(52) U.S. Cl. ......... 600/424; 600/378; 600/439; 600/468
(58) Field of Classification Search .................. 600/378, 600/468, 424
See application file for complete search history.

(56) References Cited

U.S. PATENT DOCUMENTS

| 5,127,409 | A | * | 7/1992 | Daigle ........................... 600/443 |
| 5,409,010 | A | * | 4/1995 | Beach et al. .................. 600/455 |
| 6,059,731 | A | * | 5/2000 | Seward et al. ................ 600/459 |
| 7,037,267 | B1 | * | 5/2006 | Lipson et al. ................. 600/454 |
| 2003/0011285 | A1 | * | 1/2003 | Ossmann ....................... 310/334 |
| 2003/0229331 | A1 | * | 12/2003 | Brisken et al. ................ 604/500 |
| 2005/0038343 | A1 | * | 2/2005 | Cao et al. ....................... 600/454 |
| 2006/0047333 | A1 | | 3/2006 | Tockman et al. |
| 2008/0132987 | A1 | * | 6/2008 | Westlund et al. ............. 607/122 |

FOREIGN PATENT DOCUMENTS

| DE | 69732566 | 11/1997 |
| DE | 102004062395 | 7/2006 |
| EP | 0474957 | 3/1992 |
| EP | 1 062 973 | 12/2000 |
| WO | WO 2006/116256 | 11/2006 |

OTHER PUBLICATIONS

German Search Report, dated Jan. 16, 2009.
European Search Report, dated May 15, 2009.

* cited by examiner

*Primary Examiner* — Jonathan Cwern
(74) *Attorney, Agent, or Firm* — ARC IP Law, PC; Joseph J. Mayo

(57) ABSTRACT

The invention relates to a brain stimulation electrode line (10) for electric stimulation of the brain areas with an elongated flexible electrode line body (12) having on or near its distal end at least one stimulation electrode (18) designed for delivering electric pulses to surrounding body tissue in the event of use. The brain stimulation electrode line (10) is characterized in that the electrode line body has on its distal end at least one ultrasonic transducer (20), which is arranged so that it can detect reflected ultrasound in a detection range aligned distally along the longitudinal direction of the electrode line body (12).

16 Claims, 6 Drawing Sheets

BRAIN STIMULATION ELECTRODE LINE AND INSERTION DEVICE FOR BRAIN STIMULATION ELECTRODE LINES

This application takes priority from German Patent Application DE 10 2008 015 156.4, filed 20 Mar. 2008, the specification of which is hereby incorporated herein by reference.

BACKGROUND OF THE INVENTION

1. Field of the Invention

The invention relates to a brain stimulation electrode line for stimulating deep areas of the brain. The brain stimulation electrode line has an elongated flexible electrode line body on which at least one stimulation electrode is arranged at or near its distal end. This stimulation electrode serves to deliver electric pulses to surrounding body tissue when it is used.

2. Description of the Related Art

The stimulation of deep areas of the brain is a medical treatment method for treating symptoms of Parkinson's disease, for example. Brain stimulation electrodes for deep brain stimulation (DBS) are usually implanted today by means of neuroradiological planning based on computer tomography and/or magnetic resonance imaging data. The brain stimulation electrode lines may currently be advanced only straight ahead with the help of a stereotactic target yoke. The direction of implantation is determined according to the neuroradiological planning in such a way as to prevent possible injury to intercranial blood vessels.

One disadvantage of this method is the residual risk of intracranial bleeding because the brain may shift with regard to the planned coordinates during implantation.

Another disadvantage of the implantation technique described here is that controllable brain stimulation electrode lines cannot be implanted on the basis thereof because in this case neuroradiological planning cannot be performed in real-time for all implantation feasible pathways with the controllable brain stimulation electrode line.

BRIEF SUMMARY OF THE INVENTION

The object of the invention is to provide a brain stimulation electrode line with which at least some of the disadvantages of the state of the art can be avoided.

According to the invention, this object is achieved by a brain stimulation electrode line of the type defined in the introduction, which has in the area of its distal end an ultrasonic transducer that is equipped so that it has a detection area pointing distally in the longitudinal direction of the electrode line body, i.e., looking forward in the longitudinal direction of the brain stimulation electrode line, so to speak. If necessary, multiple ultrasonic transducers, which are arranged so that some of them look straight ahead in the direction of the electrode line and others are directed obliquely, may also be provided. In any case, the brain stimulation electrode line has fewer than fifteen ultrasonic transducers.

The ultrasonic transducer(s) is/are preferably Pulse Wave Doppler sensors for detection of moving erythrocytes.

The brain stimulation electrode line is preferably connected to its insertion device, which preferably has at least one ultrasonic generator and receiver as well as a demodulator, which trigger the ultrasonic transducer to emit ultrasonic waves and which receive and demodulate the signals generated by the ultrasonic transducers due to the ultrasonic waves that are reflected and received. The demodulator is connected to a control and analyzer unit, which is designed to generate a detection signal from the demodulated ultrasonic signal, indicating whether there is a blood vessel in the detection area of the ultrasonic transducer.

The control and analyzer unit may be connected either to an optical display or an acoustic signal generator or to both.

The control and analyzer unit is preferably designed in combination with the optical display or the acoustic signal generator or both, so that the signal displayed or reproduced acoustically is different from the signal generated by the respective ultrasonic transducer, depending on the distance from the detected blood vessel. In this context, the optical display is preferably designed so that the distance from a detected blood vessel to the respective ultrasonic transducer is represented by harmless colors. In the case of the acoustic signal generator, the control and analyzer unit is preferably designed in combination with this acoustic signal generator to represent different distances between a detected blood vessel and a respective ultrasonic transducer by different sound levels.

The brain stimulation electrode line preferably comprises not just one transducer but multiple transducers, e.g., five ultrasonic transducers, one of which has a detection range aligned exactly along the extended longitudinal axis of the electrode line body, while four other ultrasonic transducers are aligned so that they each detect different sectors directed obliquely at the side.

In this case, the insertion device preferably includes a channel switch with the help of which the ultrasonic generator and receiver as well as the demodulator may optionally be connected to one of the various ultrasonic transducers. The output signals of the various ultrasonic transducers are then processed in alternation according to a type of time-multiplex method by switching the channel switch. Alternatively, each ultrasonic transducer may also be connected to a suitable ultrasonic generator and receiver. However, this would unnecessarily increase the complexity. In the case of a plurality of ultrasonic transducers and one channel switch, the control and analyzer unit is preferably connected to the channel switch and causes the connection to be switched between one ultrasonic generator and receiver and multiple ultrasonic transducers.

In the case of a plurality of ultrasonic transducers, the control and analyzer unit is also designed not only to display a signal on the optical display indicating the proximity of a blood vessel in a color-coded display but instead it additionally shows the position of a detected blood vessel relative to the lengthened longitudinal axis of the distal end of the electrode line body. For example, the optical display may be constructed so that it is subdivided into at least five display sectors, a central sector of which is surrounded by four peripheral sectors. In the central sector, a display signal obtained from the output signals of the central ultrasonic transducer is reproduced. The four other display sectors are assigned to one or more of the peripheral ultrasonic transducers. According to this latter variant of the embodiment, on insertion of the inventive brain stimulation electrode line, not only is the distance from a blood vessel taken into account but also the relative lateral position of a detected blood vessel is taken into account. This allows controlled yielding on insertion of the brain stimulation catheter and thus makes it possible to avoid intracranial; bleeding in an even more secure manner.

BRIEF DESCRIPTION OF THE DRAWINGS

The invention will now be explained in greater detail on the basis of an exemplary embodiment with reference to the figures, in which.

DETAILED DESCRIPTION OF THE INVENTION

Figure 1:
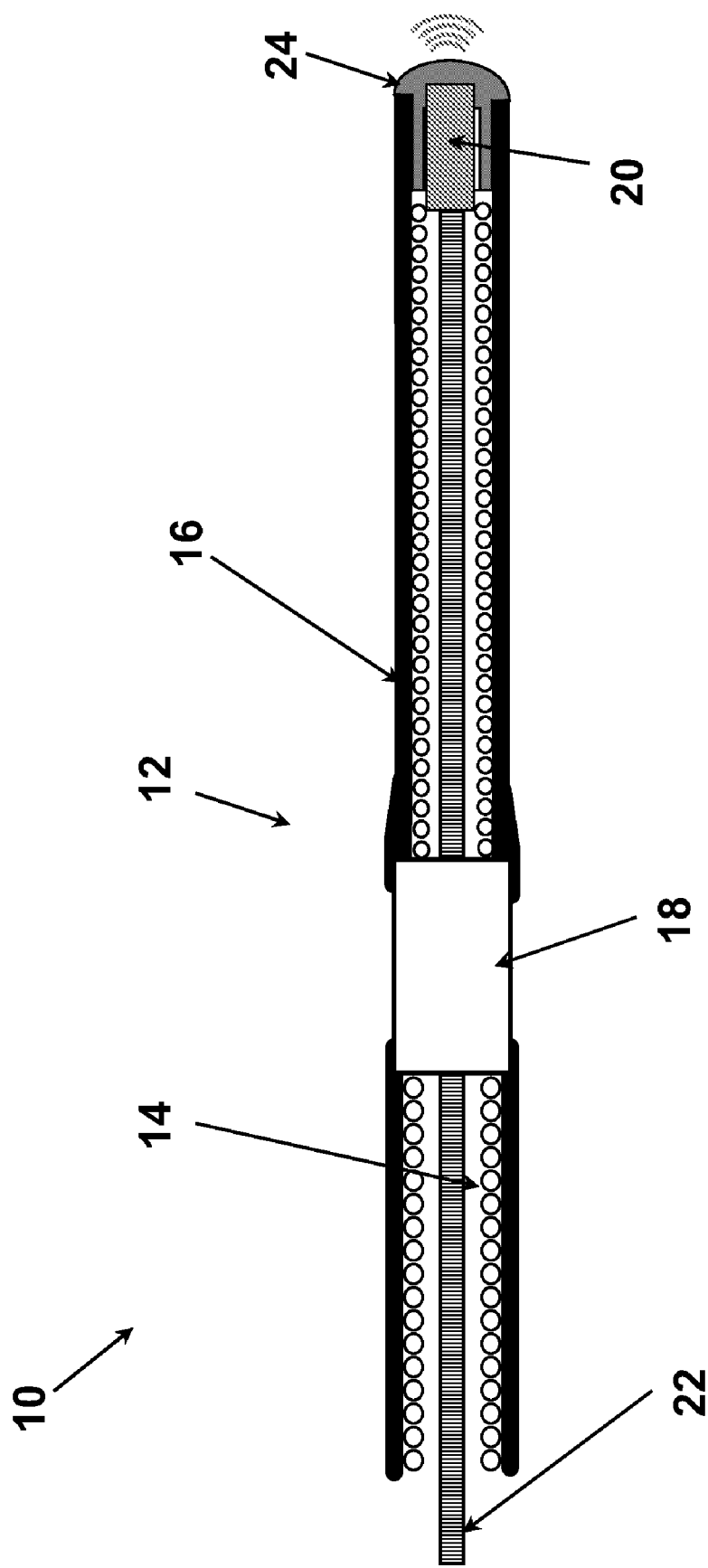
FIG. 1: shows a schematic longitudinal section through a distal end of an inventive brain stimulation electrode line.

FIG. 1 shows schematically a distal end of a brain stimulation electrode line 10 in a partially cut-away diagram. The brain stimulation electrode line 10 has an electrode line body 12, which is formed by an outer helical coil 14 made of metal and a sheathing 16 of a biocompatible plastic that surrounds the metallic helical coil 14 over most of the length of the brain stimulation electrode line 10. A ring electrode 18, which is arranged in the vicinity of the distal end of the brain stimulation electrode line 10 is not surrounded by the sheathing 16 and has an electrically conducting outside surface, which is attached to the metallic helical coil 14, so that it conducts electricity and serves to deliver stimulation pulses.

In the interior of the brain stimulation electrode line 10, an ultrasonic transducer 20 is arranged all the way at its distal end and is connected by at least one signal line 22 to a connection of the brain stimulation electrode line not shown in FIG. 1.

The ultrasonic transducer 20 is embedded in a closing body 24, which seals the brain stimulation electrode line 10 and/or its electrode line body 12 on their distal end(s). The closing body 24 is made of a biocompatible material that allows input and output coupling for transmission of ultrasonic waves with low damping. The shape of the closing body is adapted to the shape of the ultrasonic transducer 20, so the ultrasonic transducer 20 and the closing body 24 are in contact over a large area.

Figure 2:
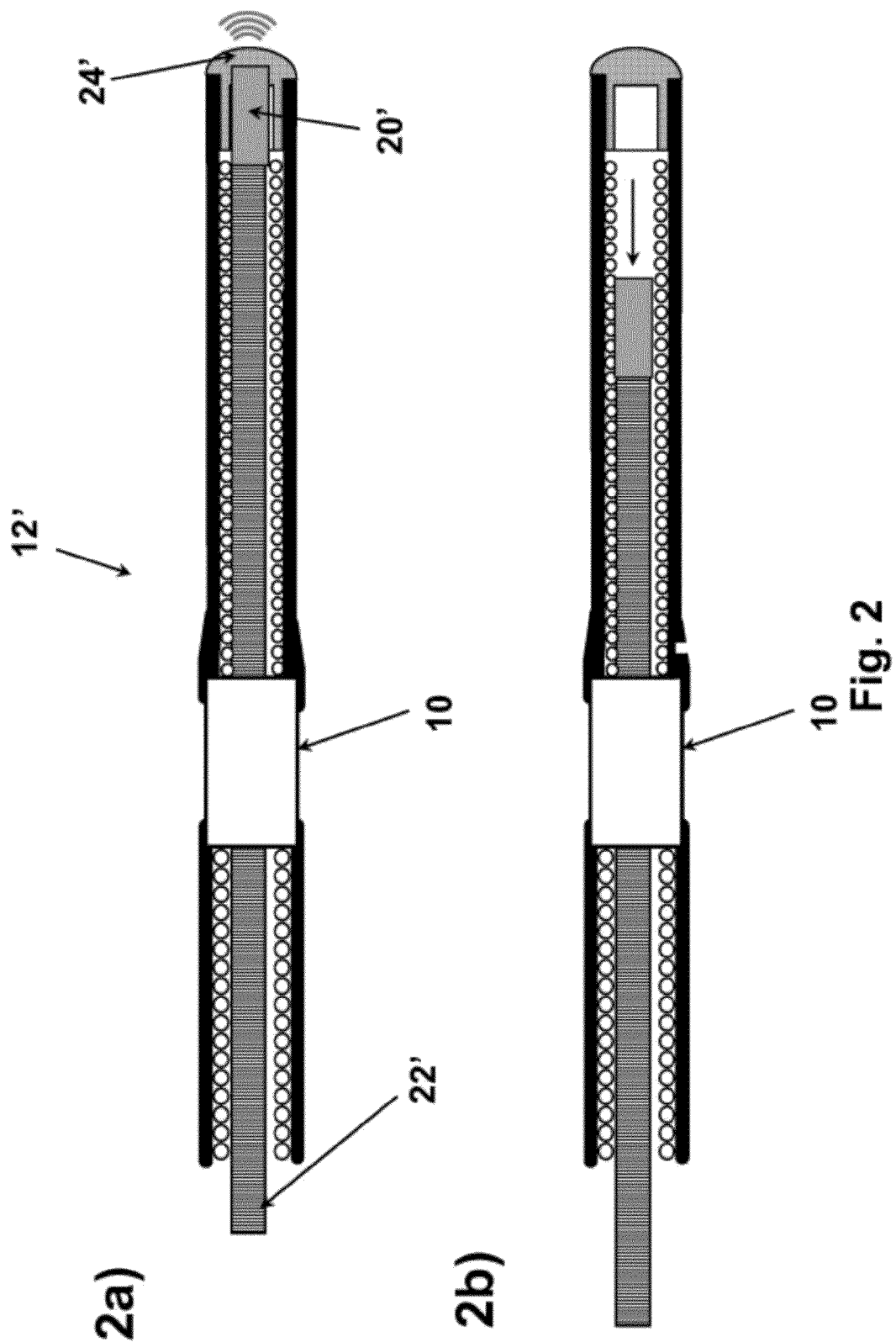
FIGS. 2a and 2b: show a schematic longitudinal section through a distal end of an alternative variant of an exemplary embodiment of a brain stimulation electrode line.

FIGS. 2a and 2b show a preferred variant of the embodiment in which the ultrasonic transducer 20' and the signal line 22' are guided in a lumen of the electrode line body 12 so that they are movable longitudinally. The signal line 22' is therefore designed as a removable mandrel. FIG. 2a shows the ultrasonic transducer 20' and the signal line 22' in the state in which they are completely inserted into the lumen of the electric line body 12', with at least one front surface of the ultrasonic transducer 20' being in flush contact with an inside surface of the closing body 24'. FIG. 2b shows how the ultrasonic transducer 20' can be removed from the lumen of the electrode line body 12' together with the signal line 22'. The signal line 22' is therefore embedded in the mandrel, which is labeled with the same reference numeral 22'. This mandrel 22' may even contain multiple signal lines and may therefore also be referred to as a signal line body.

All these embodiments have in common the fact that the brain stimulation electrode line for deep brain stimulation and one or more ultrasonic transducers are arranged either in surface contact or on a hemisphere in the probe body of the brain stimulation electrode line itself or at the tip of a guide catheter, such that the detection ranges of the ultrasonic transducers are directed in the distal direction of the brain stimulation electrode line.

Figure 3:
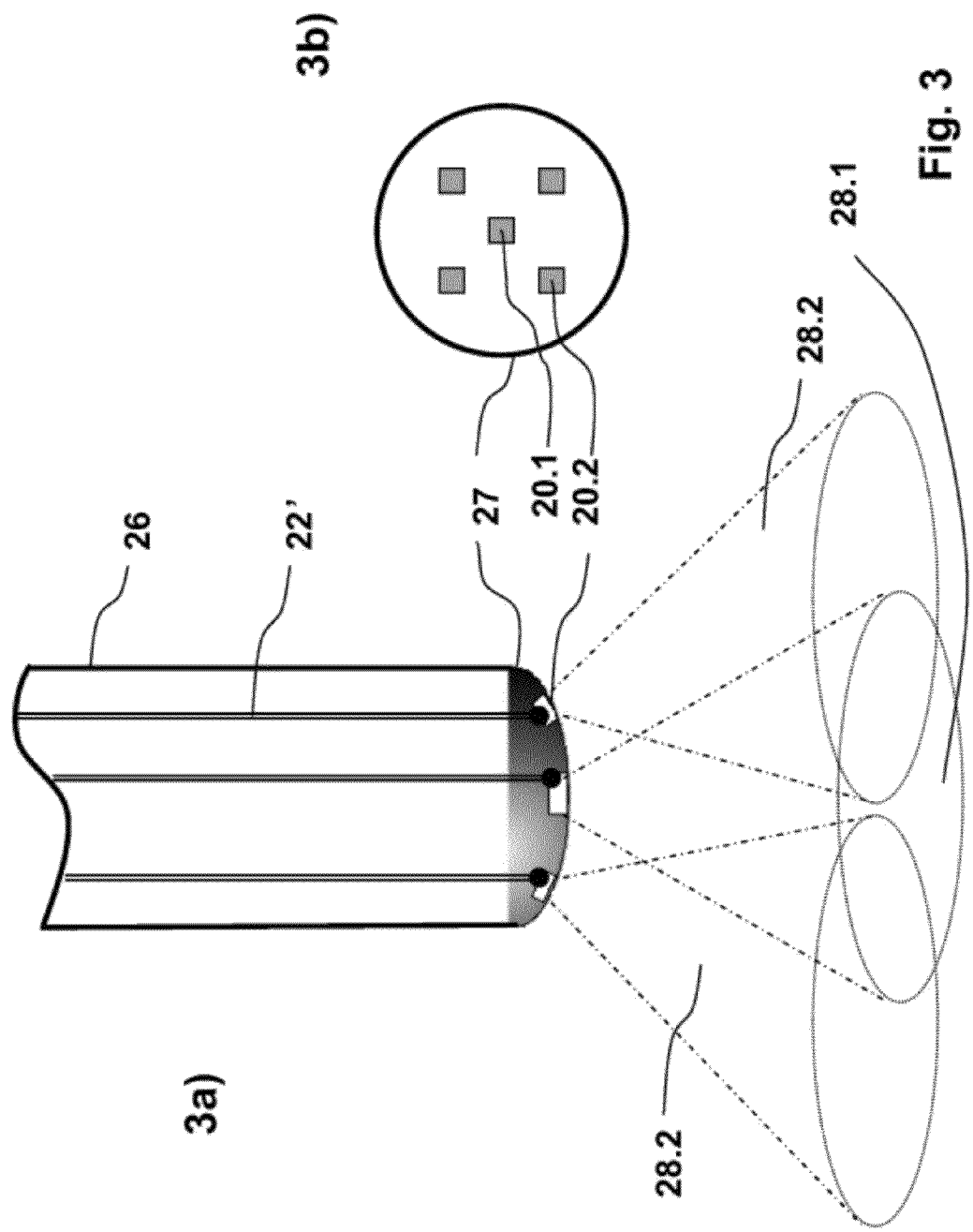
FIGS. 3a and 3b: show details of a variant of the embodiment of a brain stimulation electrode line having a plurality of ultrasonic transducers in a schematic diagram.

FIGS. 3a and 3b show one possible arrangement of five ultrasonic transducer crystals 20 as ultrasonic transducers, which are arranged on a convex carrier 27 in the tip of a brain stimulation electrode line 10, so that it is possible to look to the right and obliquely forward from the respective ultrasonic transducers 20.1 and 20.2.

FIG. 3a here shows the distal end of a preferred variant of an embodiment of such a signal line body 26 with signal lines 22' which are embedded therein and are connected at their respective distal ends to a respective ultrasonic transducer 20.1 or 20.2. The ultrasonic transducers 20.1, 20.2 are embedded in an end face of the signal line body 26, so that they form a central ultrasonic transducer 20.1 in a view of the end face (FIG. 3b) as well as forming four peripheral ultrasonic transducers 20.2 distributed uniformly around it.

As shown in FIG. 3a, the central ultrasonic transducer 20.1 is oriented so that the detection range 28.1 is aligned concentrically with the lengthened longitudinal axis of the signal line body 26, while the peripheral ultrasonic transducers 20.2 are arranged so that their detection ranges 28.2 are each aligned obliquely forward.

The signal line body 26 with a total of five ultrasonic transducers 20.1 and 20.2 may be inserted into the lumen of an electrode line body 12', as illustrated in FIGS. 2a and 2b, in such a way that the convex end face of the signal line body 26 is in flush contact with a corresponding concave inside surface of a correspondingly shaped closing body. This forms a brain stimulation electrode line having five ultrasonic detection channels. In one or more embodiments, the elongated flexible electrode line body has a maximum outside diameter of 1 mm on a length of the elongated flexible electrode line body that is intended for implantation The ultrasonic transducers 20 are each Pulse Wave Doppler sensors, which are designed to detect moving erythrocytes according to the Doppler principle, which is already known per se. In this way, blood vessels in the detection area of a respective ultrasonic transducer 20 can be detected with the help of the ultrasonic transducers 20.

This allows detection of blood vessels upstream from the distal end of the brain stimulation electrode line 10 when the latter is to be inserted up to a respective stimulation site.

Figure 4:
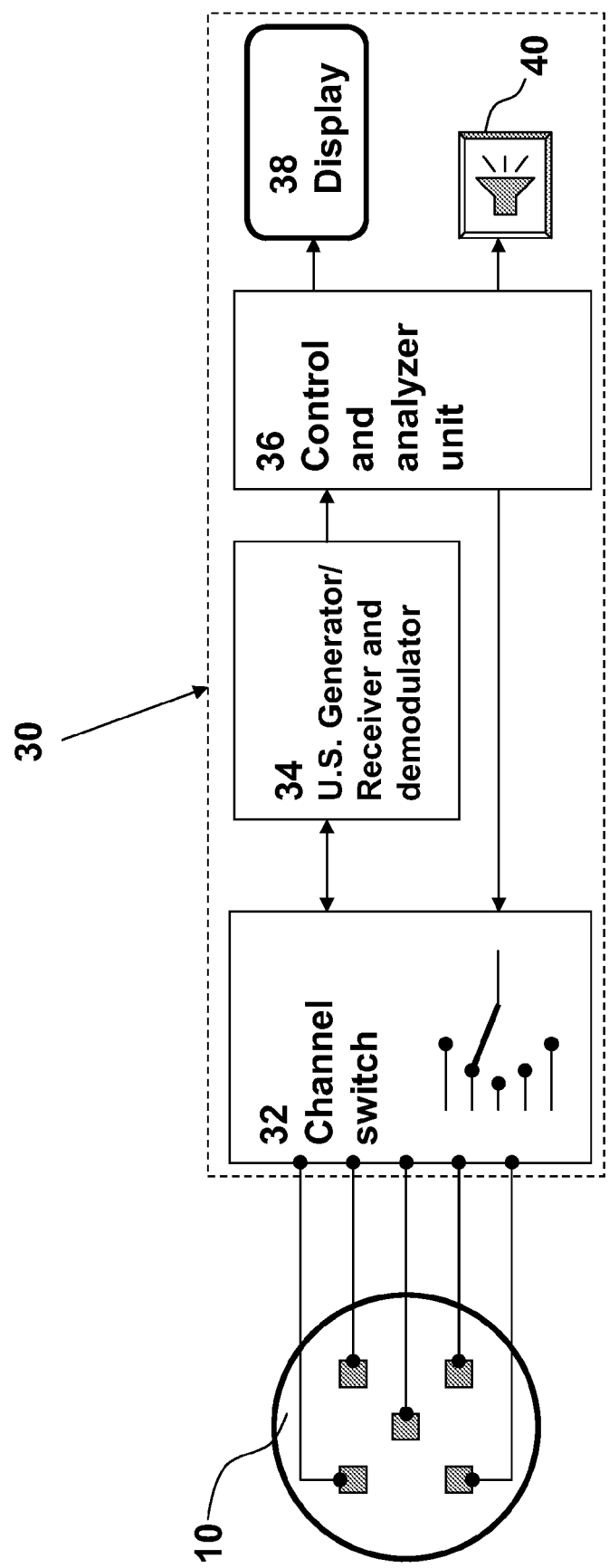
FIG. 4: shows a basic diagram of an insertion device for a brain stimulation electrode line 10 according to the invention.

To do so, the ultrasonic transducers 20 of the brain stimulation electrode line 10 are connected to an insertion device, which is diagrammed schematically in FIG. 4 and has a signal processing unit 30 next to the brain stimulation electrode line 10. First it includes a channel switch 32 to optionally send the signals originating from the respective ultrasonic transducer 20 to an ultrasonic generator and receiver as well as a demodulator 34, whose output values are in turn sent to a control and analyzer unit 36. This control and analyzer unit 36 also controls the channel switch 32. Furthermore, the control and analyzer unit 36 is connected to a graphic display 38 and to an acoustic signal generator 40.

The ultrasonic generator 34 generates ultrasonic pulses whose frequency and ultrasonic energy are adapted for intracerebral use, such that a blood vessel running at a distance of 0-50 mm upstream from the distal end of the brain stimulation electrode line 10 can be evaluated there.

The control and analyzer unit 36 is designed in connection with the optical display 38 and/or the acoustic signal generator 40, so that the respective signal displayed and/or reproduced acoustically is different, depending on the distance between the detected blood vessel and the respective ultrasonic transducer 20. The loudness of the signal reproduced acoustically may depend on distance, for example. Even better, the acoustic signals depends on distance with regard to the tone pitch, such that high tones characterize a short distance and low-frequency tones characterize a greater distance. No acoustic signal at all is an indication that there are no blood vessels in the detection area of the ultrasonic transducer or transducers.

When the signal processing unit 30 detects a blood vessel in the forward direction of an ultrasonic transducer, the control and analyzer unit 36 determines the distance from this blood vessel and initiates an optical signal and an acoustic signal with which the user is notified of the distance from the detected blood vessel. The optical display 38 also supplies in addition to the distance information, information about the direction in which a blood vessel has been detected by the fact that a separate optical display element, e.g., in the form of a sector of the optical display 38 (see further below) for each ultrasonic transducer 20. For example, this display element may be green, according to the distance (no blood vessel ahead), yellow (blood vessel ahead at a distance of a-b mm) or red (blood vessel immediately ahead).

Similarly, the acoustic signal generator 40 may also be controlled in such a way that it receives information about the direction in which a blood vessel has been detected. The repetition frequency of an interrupted acoustic signal is increased in inverse proportion to the distance from the blood vessel. If the blood vessel is directly ahead, then a continuous tone is delivered.

The user can individually define the ranges for the various warning levels (green, yellow, red) in the analyzer unit 36.

The optical display 38 is preferably constructed as shown in FIG. 5. It has a central sector 42, which is assigned to the central transducer 20.1 and a total of four peripheral sectors 44, each being assigned to one of the peripheral transducers 20.2. The sectors are each divided into subsectors and the optical display 38 is designed in conjunction with the control and analyzer unit 36, so that the number of subsectors controlled is greater, the closer a respective detected blood vessel is to the respective transducer. A blood vessel entering the detection range of the central ultrasonic transducer 20.1 results in only a central subsector of the central sector 42 being controlled, i.e., being shown in black, for example. More subsectors of the central sector 42 are controlled as the detected blood vessel is closer to the central ultrasonic transducer 20.1.

Accordingly, the control and analyzer unit 36 is designed in conjunction with the optical display 38 and the subsectors of the peripheral sectors 44 are also to be triggered as a function of the distance between a blood vessel and the respective ultrasonic transducer to be detected. If the detected blood vessel is still at a great distance from the respective ultrasonic transducer 20.2, then only the internal subsector of the respective peripheral sector 44 is triggered. With increasing proximity, additional subsectors of the peripheral sector 44 are activated gradually from the inside to the outside, e.g., they are shown as being dark in the illustration in FIG. 5b as an example. Such a display allows an intuitive estimation of the respective situation prevailing upstream from the distal end of the brain stimulation electrode line.

Figure 5A:
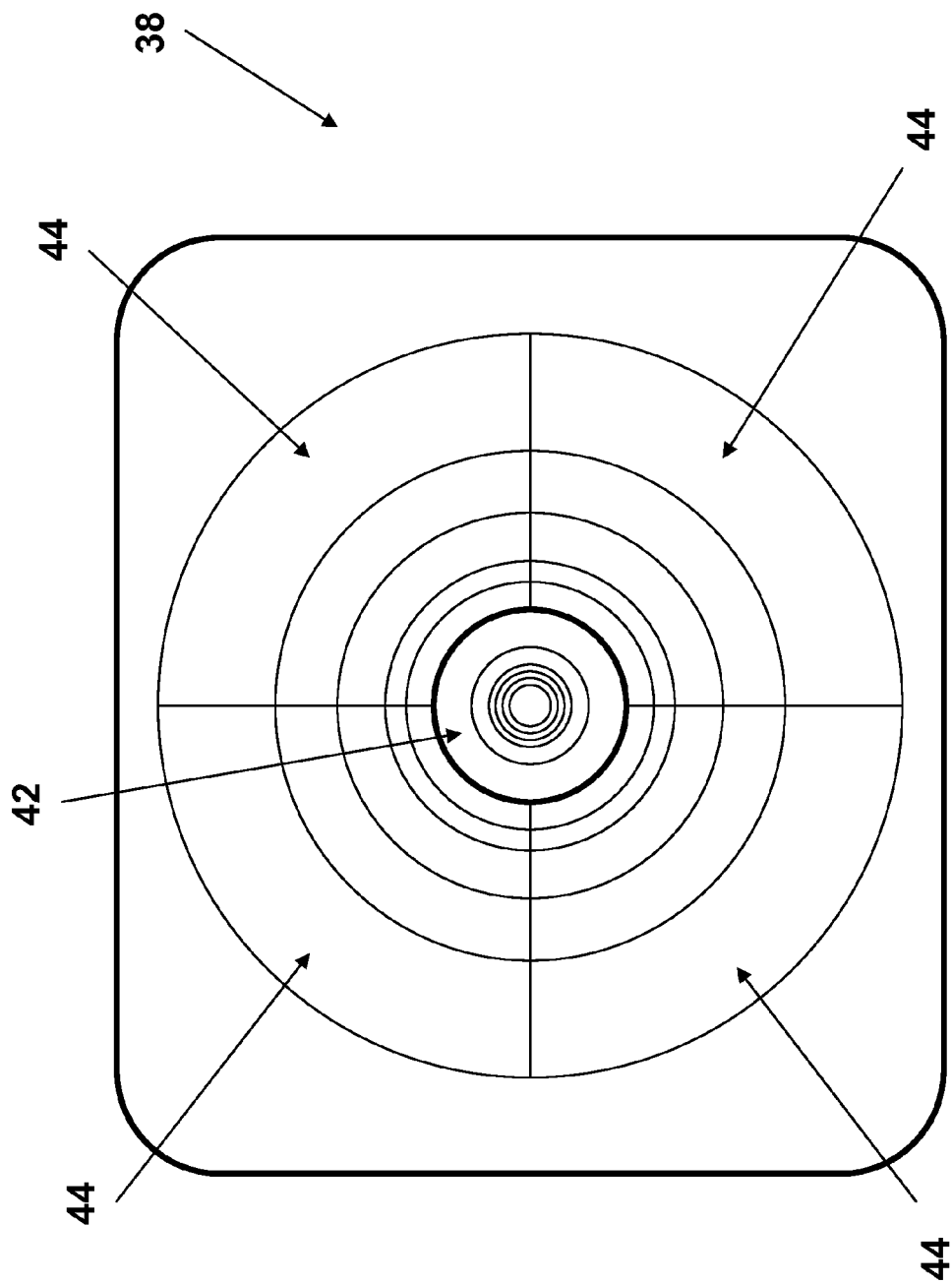
FIGS. 5a and 5b: show a diagram of an optical display for the insertion device according to FIG. 3.
Figure 5B:
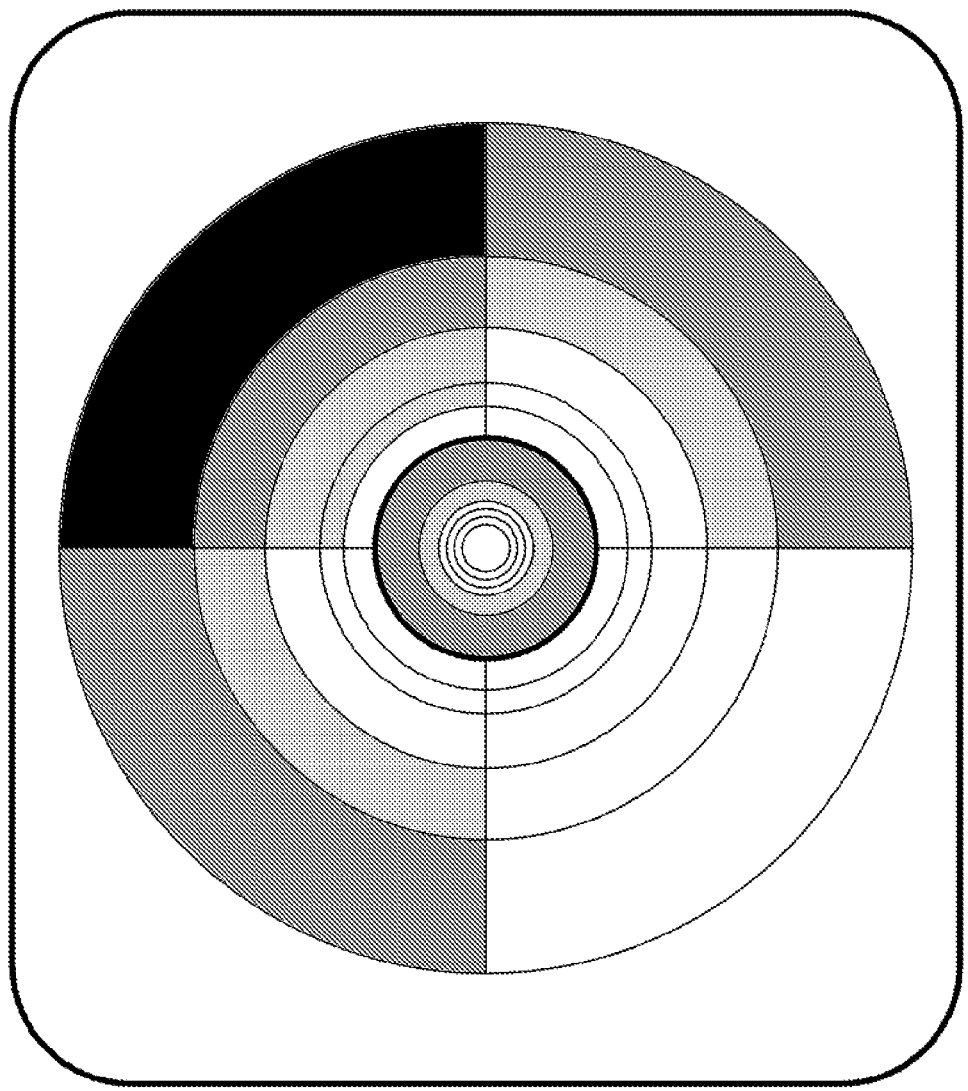

FIG. 5b shows the possible display of the distance information with the optical display 38 having five sectors (four quadrants=obliquely forward, one center=forward right) according to FIG. 5a. Each sector is divided into subsectors and indicates the distance from a blood vessel directly ahead in the direction of the ultrasonic transducer assigned to the respective sector 42 or 44 of the display 38 using the colors white=no Doppler signal, green=weak signal, yellow=medium signal, red=strong signal.

What is claimed is:

1. An apparatus for electric stimulation of deep brain areas comprising:
   a brain stimulation electrode line (10) comprising
      an elongated flexible electrode line body (12) coupled with a convex carrier (27) on a distal end of the elongated flexible electrode line body and at least one stimulation electrode (18) near said distal end which is configured to deliver electric pulses to body tissue during use;
   at least one ultrasonic transducer (20) up to maximally fifteen ultrasonic transducers comprising
      a central ultrasonic transducer (20.1) coupled with the convex carrier and aligned concentrically to point in a forward direction along a longitudinal direction of the elongated flexible electrode line body (12) and
      four peripheral ultrasonic transducers (20.2) coupled with the convex carrier and aligned to point obliquely forward in four different directions and
      wherein said central and four peripheral ultrasonic transducers (20.1, 20.2) are arranged to detect reflected ultrasound in a detection range which is oriented distally in five different directions and are further configured to detect reflections of ultrasonic waves that are characteristic of intercranial blood vessels; and,
   an insertion device for brain stimulation electrode lines coupled with said brain stimulation electrode line (10) and comprising
      a signal processing unit (30) comprising
         a control and analyzer unit (36), which is connected at least indirectly to the central and four peripheral ultrasonic transducers (20.1, 20.2) each of which are configured to generate a signal which indicates a distance to a detected blood vessel, and a relative lateral position of said detected blood vessel relative to a lengthened longitudinal axis of the distal end of the elongated flexible electrode line body (12) wherein the control and analyzer unit (36) is configured to determine the distance to and relative lateral position of said detected blood vessel in relation to the elongated flexible electrode line body (12) based on the generated signals;
         a display unit (38, 40) coupled with said control and analyzer unit (36) and comprising an optical display configured to display information associated with said distance from said detected blood vessel and said relative lateral position of said detected blood vessel obtained from said central and said four peripheral ultrasonic transducers in five display sectors (42, 44) respectively that correspond to said forward direction and said four different directions wherein said five display sectors comprise different areas on said optical display wherein said display of said information occurs during insertion of said brain stimulation electrode line in order to avoid intracranial bleeding.

2. The apparatus according to claim 1, wherein the at least one ultrasonic transducer (20.1, 20.2) is connected to at least one electric line which is guided as a signal line (22) to a proximal end of the elongated flexible electrode line body (12) and wherein the at least one electrical line is configured to transmit detection signals to a connection at the proximal end of the elongated flexible electrode line body (12), wherein said detection signals are generated by a respective ultrasonic transducer on reception of reflected ultrasonic waves.

3. The apparatus according to claim 2, wherein the at least one electrical line is part of a line body fixedly connected to the at least one ultrasonic transducer, which is longitudinally movable inside of the elongated flexible electrode line body.

4. The apparatus according to claim 1, wherein the at least one ultrasonic transducer (20.1, 20.2) is fixedly connected to the elongated flexible electrode line body (12) and is arranged in an area of the distal end of the elongated flexible electrode line body (12).

5. The apparatus according to claim 1, wherein the elongated flexible electrode line body (12) has a lumen into which the at least one ultrasonic transducer is removably inserted.

6. The apparatus according to claim 5, wherein the lumen in the elongated flexible electrode line body is closed at the distal end by a closing body (24) made of a material which allows input and output coupling as well as transmission of ultrasonic waves with minor damping and which has, on an inside face of the closing body (24), a shape that corresponds to the shape of the at least one ultrasonic transducer at the distal end.

7. The apparatus according to claim 1, wherein the elongated flexible electrode line body (12) comprises up to ten additional ultrasonic transducers aligned to point in other different directions than said different direction so that said elongated flexible electrode line body (12).

8. The apparatus according to claim 1, wherein the at least one ultrasonic transducer is a Pulse Wave Doppler ultrasonic transducer configured to detect erythrocytes that move.

9. The apparatus according to claim 1, wherein the at least one ultrasonic transducer is or are connected to electric lines, which are guided as signal lines to a proximal end of the elongated flexible electrode line body (12) and wherein the electric lines are configured to transmit detection signals that are generated when reflected ultrasonic waves are received.

10. The apparatus according to claim 1, wherein the elongated flexible electrode line body (12) has a maximum outside diameter of 1 mm on a length of the elongated flexible electrode line body (12) that is intended for implantation.

11. The apparatus according to claim 1, further comprising an acoustic signal generator (40) coupled with said control and analyzer unit and configured to acoustically reproduce said position of said detected blood vessel to a respective ultrasonic transducer (20.1, 20.2).

12. The apparatus according to claim 11, wherein the display unit is configured to display said distance of the detected blood vessel from said central and said four peripheral ultrasonic transducers (20.1, 20.2) in different colors.

13. The apparatus according to claim 11, wherein the acoustic signal generator (40) is configured such that different distances between the detected blood vessel and the respective ultrasonic transducer (20.1, 20.2) are reproduced by different tone pitches or tone amplitude levels.

14. The apparatus according to claim 1, wherein the signal processing unit (30) comprises a channel switch (32) and an ultrasonic generator and receiver (34) coupled with said channel switch, wherein the channel switch (32) is connected to the at least one ultrasonic transducer (20.1, 20.2) and the ultrasonic generator and receiver (34) is coupled with the control and analyzer unit, such that the ultrasonic generator and receiver (34) is connected to one of the at least one ultrasonic transducer in a time multiplexed manner.

15. The apparatus according to claim 14, wherein the ultrasonic generator and receiver (34) is configured to generate and receive ultrasonic pulses whose frequency and ultrasonic energy are configured for intracerebral use, such that a blood vessel can be evaluated at a distance of 0-50 mm upstream from the distal end of the elongated flexible electrode line body (12).

16. The apparatus according to claim 1, wherein the five display sectors (42, 44) are subdivided into subsectors, and the control and analyzer unit (36) is configured in conjunction with the optical display (38) to control the subsectors as a function of the distance from the detected blood vessel which the control and analyzer unit (36) has determined for the respective ultrasonic transducer.

* * * * *